Dec. 9, 1952 L. VISTICA Plant Pat. 1,153
PEAR TREE
Filed Oct. 19, 1951
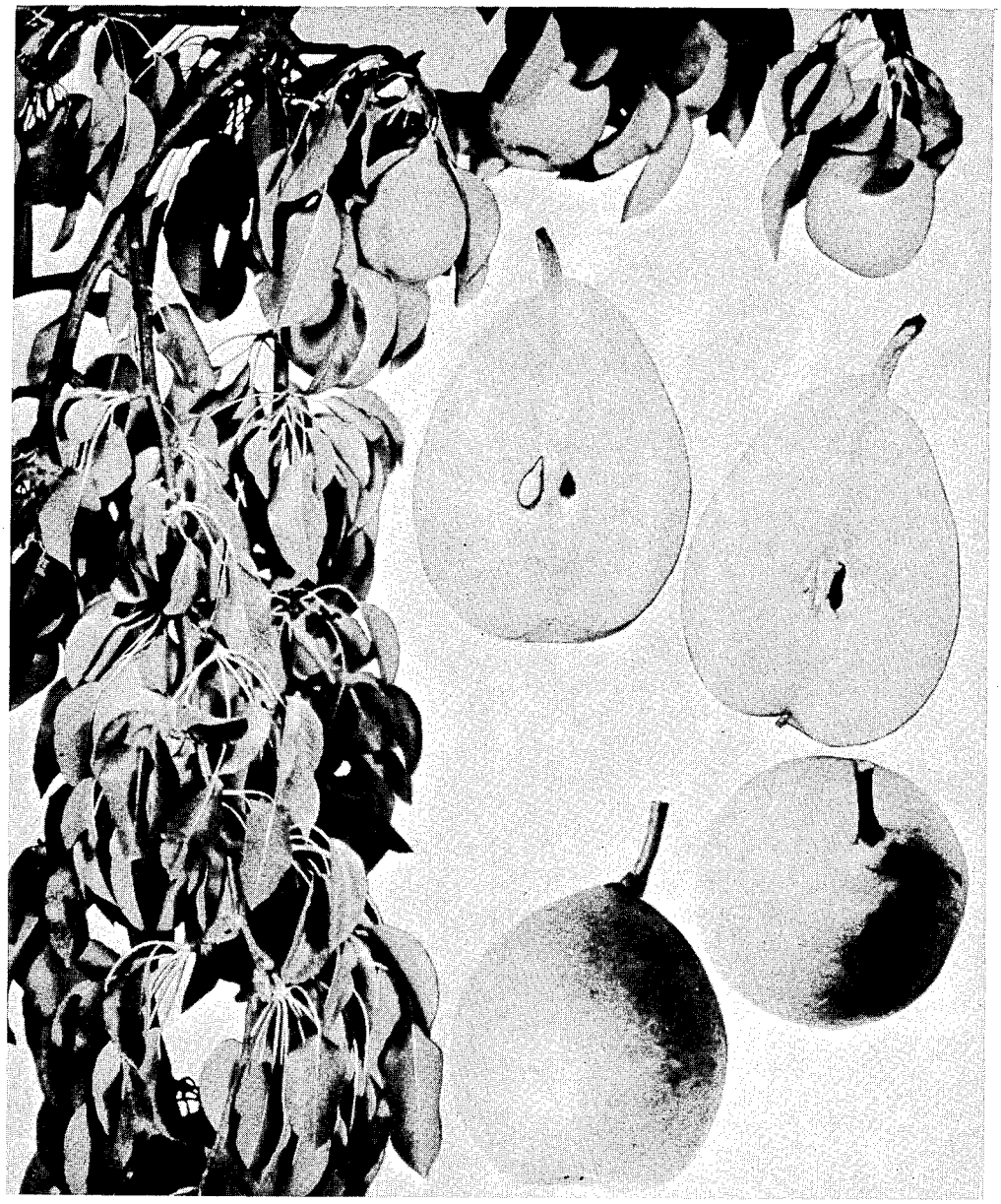
Inventor.
Louis Vistica
By: Robbins Robb
Attorneys.

Patented Dec. 9, 1952

Plant Pat. 1,153

UNITED STATES PATENT OFFICE 1,153

PEAR TREE

Louis Vistica, Yuba City, Calif.

Application October 19, 1951, Serial No. 252,015

1 Claim. (Cl. 47—62)

The present invention relates to a new and distinct variety of pear tree originated by me by crossing the variety "Burkett" (unpatented) × the variety "Farmingdale" (unpatented). This new variety is characterized as to novelty by the combination of the following characteristics which distinguish it from its parents, as well as from all other varieties:

(1) Its high resistance to *Phytomonas amylovora* or "fire blight," particularly in the west coast region of the United States, where pear trees of the "Bartlett" variety are killed by blight. The present variety has failed to take artificial inoculation with pear blight over a period of years;

(2) Its strong, vigorous habits of growth even in shallow, heavy soil;

(3) Its consistent, heavy production of uniform and symmetrical fruit, without thinning averaging 2⅜ inches in diameter, and with thinning and pruning average 2¾ inches in diameter; and (4) The smooth texture of the flesh and the juiciness and sweet flavor of the fruit.

As compared with its parent variety "Burkett," this new variety bears larger, more symmetrical fruit having a smoother flesh than "Burkett," and this new variety has retained the vigorous growing habits of "Burkett" which is a vigorous grower.

As compared with its other parent "Farmingdale," this new variety bears fruit approximately the same size as "Farmingdale," but the fruit of the new variety is more symmetrical and has flesh of a smoother texture, the flesh being more juicy and having a finer and sweeter flavor than does the fruit of "Farmingdale." Moreover, the present variety is a much stronger growing variety than "Farmingdale."

Asexual reproduction of this new variety by grafting and budding near Yuba City, California, shows that the foregoing characteristics are established and come true to form and are transmitted through succeeding propagations.

The accompanying drawing shows a typical limb section of one of my new pear trees, with typical foliage and fruit borne thereby, and also shows enlarged views of specimens of the fruit, with the fruit illustrated respectively in top plan, side elevation and in section through the axial center thereof to expose the core and the seeds thereof.

The following is a detailed description of my new variety, with color terminology in accordance with ordinary dictionary significance:

Parentage: Seedling.
*Male.*—"Burkett."
*Female.*—"Farmingdale."

Where specimens were grown and observed: Near Yuba City, California.

Dates first and last picking: August 1st to 15th.

*Tree*

Medium size; vigorous; upright, partially spreading; tall; vase formed; medium growing; hardy; very productive; regular bearer.

Trunk: Medium size; medium smoothness.

Branches: Medium thickness; medium smoothness; much branched; green-brown.
*Lenticels.*—Medium number; medium size.

Leaves:
*Length.*—2½ to 3 inches.
*Width.*—1½ to 2 inches.
Small to medium in size; medium width; medium length; oval; abruptly pointed; medium thickness; medium green; smooth.
*Margin.*—Very finely crenate.
*Petiole.*—Length, 1¼ to 2 inches; medium to long; slender.

Flowers: Dates of first and full bloom—March 15th to April 1st. Medium early; medium size; white.

*Fruit*

Maturity when described: Eating ripe. Date—August 8th.

Size: Uniform.
*Axial diameter.*—2½ to 3 inches.
*Transverse diameter.*—2⅜ to 2½ inches.
*Shape.*—Obovate, with a rounded neck; somewhat variable; short to medium length; truncate at apex.

Cavity: Lacking.

Basin:
*Depth.*—$\frac{3}{16}$ to ¼ inch.
*Breadth.*—⅞ inch.
*Markings.*—Slightly furrowed.
Symmetrical; rounded; base wide; undulate; glabrous.

Stem: Medium thickness; glabrous; a few scattered, light-colored lenticels; slightly lipped at base.
*Length.*—¾ to ⅞ inch.
*Breadth.*—⅛ inch.

Calyx: Open; segments persistent; lanceolate; obtuse; length ⅛ inch; separated at base: reflexed from base at apex; outer and inner surfaces pubescent.

Eye: Large size; open.

Skin: Thick; tough; smooth; glossy; waxed.
*Dots.*—Obscure; many; small; even; circular.
*Color of dots.*—Brown.
*Distribution of dots.*—Even.
*Scarfskin.*—Wanting.
*Bloom.*—Wanting.
Flesh: Juicy.
*Color of flesh.*—White.
*Texture.*—Firm; tender; melting.
*Flavor.*—Mild; sweet; delicate.
*Quality.*—Good.
Core: Distant.
*Bundle area.*—Small to medium; narrowly ovate; symmetrical; acute at base.
*Halves of area.*—Equal.
*Bundles.*—Green; inconspicuous; in one whorl.
*Alternate bundle.*—Reaches tube below stamens.
*Core lines.*—Clasping.
*Carpellary area.*—Indistinct; small.
*Calyx tube.*—Glabrous; cone-shaped.
*Stem of funnel.*—Short.
*Depth of tube to shoulder.*—⅛ inch.
*Styles.*—Present; distinct toward base; glabrous throughout.
*Stamens.*—In one whorl; marginal.
*Axillary cavity.*—Present.
*Seed cells.*—Axile; closed.
*Cell walls.*—Approximate; thin; tender. Length, ½ inch. Breadth, ¼ inch.
*Longitudinal section.*—Narrowly obovate; obtuse at apex.
*Surface.*—Smooth.
*Cross section.*—Broad.
Seeds:
*Number.*—Perfect, 7 to 9; imperfect, 1 to 3; largest, 10. Number in one cell, 2; length ⅜ inch; breadth $\frac{3}{16}$ inch.

*Form.*—Acuminate to acute.
*Color.*—Light brown to black, changing color at maturity.
Use: Market.
Keeping quality: Medium. Number of days in ordinary storage, 30.
Resistance to:
*Insects.*—Medium. The tree and fruit of this variety react to attack by commonly occurring insects, such as thrips or European red spider, essentially the same as the "Bartlett" variety, when growing under comparable cultural conditions, and when sprayed to control such insects.
*Diseases.*—Medium, but blight resistant. This new variety has medium resistance to diseases generally, as compared with other varieties grown under the same conditions, but it is completely resistant to blight, such as *Phytomonas amylovora* or "fire blight," as proven by attempts at artificial inoculation of the new variety by placing bud wood having blight into openings in the cambium of a tree of my new variety. Such attempts at inoculation were made over a number of years during the season when the disease is most virulent.

I claim:

A new and distinct variety of pear tree, substantially as herein shown and described, characterized as to novelty particularly by its strong blight resistance, by its strong and vigorous habits of growth, and by its consistent heavy production of relatively large, uniform and symmetrical fruit having very juicy flesh of smooth texture and very sweet flavor.

LOUIS VISTICA.

No references cited.